Figure 1:
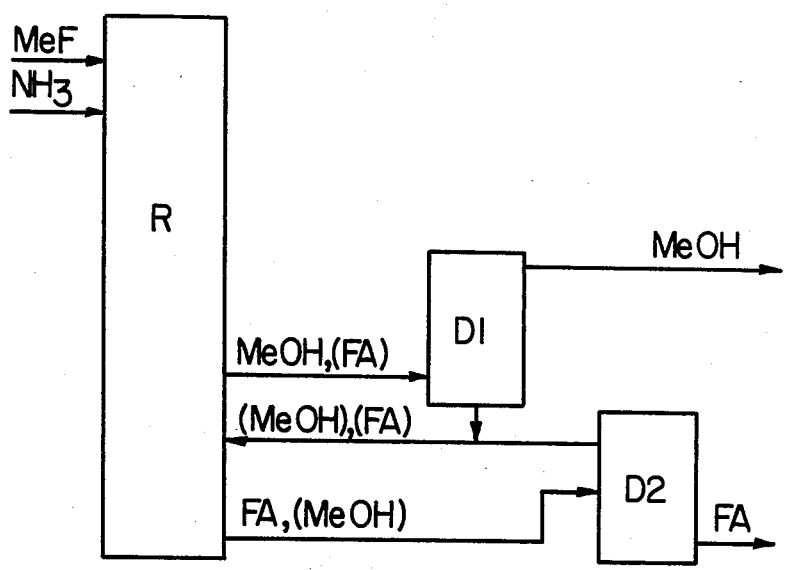

United States Patent [19]

Bott et al.

[11] Patent Number: 4,659,866

[45] Date of Patent: Apr. 21, 1987

[54] CONTINUOUS PREPARATION OF FORMAMIDE

[75] Inventors: Kaspar Bott, Wachenheim; Gerd Kaibel, Lampertheim; Herwig Hoffmann, Frankenthal; Rudolf Irnich, Bobenheim; Otto Kratzer, Bobenheim-Roxheim, all of Fed. Rep. of Germany

[73] Assignee: BASF Aktiengesellschaft, Fed. Rep. of Germany

[21] Appl. No.: 347,578

[22] Filed: Feb. 10, 1982

[30] Foreign Application Priority Data

Feb. 19, 1981 [DE] Fed. Rep. of Germany ....... 3106054

[51] Int. Cl.$^4$ ............................................ C07C 102/06
[52] U.S. Cl. .................... 564/137; 564/141; 568/918
[58] Field of Search ................. 564/137, 141; 568/918

[56] References Cited

U.S. PATENT DOCUMENTS

| 2,106,579 | 1/1938 | Tanner | 564/137 |
|---|---|---|---|
| 3,072,725 | 1/1963 | Surman | 564/137 |
| 3,324,179 | 6/1967 | Scholz et al. | 564/137 |
| 3,342,862 | 9/1967 | Board, Jr. et al. | 564/137 |

FOREIGN PATENT DOCUMENTS 1215130 11/1966 Fed. Rep. of Germany .

OTHER PUBLICATIONS

Ullmanns Encyklop. der Tech. Chemie, 4th Ed., vol. II, pp. 703–710.

Primary Examiner—Robert V. Hines
Attorney, Agent, or Firm—Keil & Weinkauf

[57] ABSTRACT

Formamide is prepared continuously from methyl formate and ammonia, pure methanol being recovered, by a process wherein (a) the reaction of methyl formate and ammonia is carried out predominantly in the liquid phase in the upper region of a reaction column R having a total of from 15 to 30 theoretical plates, (b) the methanol formed in this reaction is removed, together with small amounts of formamide, from the column or the evaporator in vaporus form at the level of plates 1–5 (counted from the bottom), (c) the formamide is removed from this methanol/formamide mixture, together with small amounts of methanol, in a distillation column D1 and recycled to R, and (d) the small amounts of methanol contained in the bottom product from R, which substantially consists of formamide and in this column should be at from 110° to 130° C., are separated off in a distillation column D2.

2 Claims, 2 Drawing Figures

MeF = METHYL FORMATE
MeOH = METHANOL
FA = FORMAMIDE
( ) = MINOR AMOUNTS

CONTINUOUS PREPARATION OF FORMAMIDE

The present invention relates to an improved process for the continuous preparation of formamide by reacting methyl formate with ammonia:

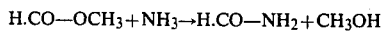

Apart from the improvement according to the invention, this reaction is generally known, but in practice it is beset with considerable difficulties since it has not yet been possible economically to recover the methanol in a sufficiently pure form for it to be recycled to the methyl formate synthesis without further treatment (cf. for example, Ullmanns Encyklopädie der technischen Chemie, 4th edition (1976), volume 11, page 704).

German Pat. No. 1,215,130 discloses a process in which the problem of recovering pure methanol is solved by vaporizing all the components of the aminolysis mixture except for the formamide and fractionally liquefying the methanol from the vapor. However, this procedure is technologically involved and is also unsatisfactory in respect of the purity of the methanol, which still contains from about 500 to 800 ppm of bonded nitrogen.

It is an object of the present invention to improve the technological and economic aspects of the preparation of formamide from methyl formate and ammonia.

We have found that this object is achieved and that formamide is obtained from methyl formate and ammonia, pure methanol being recovered, in a technologically elegant manner when (a) the reaction of methyl formate and ammonia is carried out predominantly in the liquid phase in the upper region of a reaction column R having a total of from 15 to 30 theoretical plates, (b) the methanol formed in this reaction is removed, together with small amounts of formamide, from the column or the evaporator in vaporous form at the levels of plates 1–5 (counted from the bottom), (c) the methyl formate is removed from this methanol/formamide mixture, together with small amounts of methanol, in a distillation column D1 and recycled to R, and (d) the small amounts of methanol contained in the bottom product from R, which substantially consists of formamide and in this column should be at from 110° to 130° C., are separated off in a distillation column D2.

Figure 2:
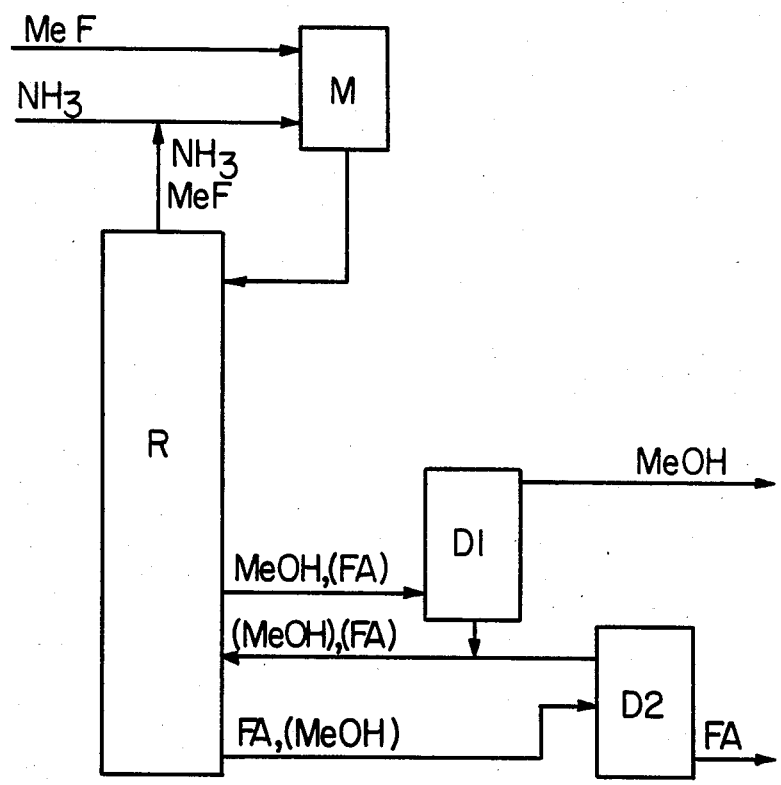

FIG. 1 illustrates this process and FIG. 2 shows a preferred technological embodiment in which methyl formate and ammonia are mixed, before entry into the column R, in a mixing chamber M to which the vapors leaving R can be recycled, if necessary via a compressor (not shown in the Figure).

The central feature of the process according to the invention is the reaction column R and the temperature gradient maintained therein, which, under atmospheric pressure, ranges from 30°–62° C. at the top of 110°–130° C. at the bottom. In industry, this column is preferably operated under slightly increased pressure—up to about 2 bar—because this enables the top of the column to be cooled with normal cooling water. For example, the top of the column is at 50°–80° C. under 2 bar.

Preferred designs of column R are those in which relatively long residence times can be established at the individual trays, and at least in the region of the top 5 trays. Accordingly, all the conventional industrial embodiments of valve trays or, in particular, bubble trays can be used. In contrast, layers of packing are more advantageous for the middle and lower regions of the column, since in these regions backreaction of the formamide to give ammonia is to be suppressed by means of very low residence times of the liquid.

In process step (a), methyl formate and gaseous or liquid ammonia are introduced, preferably in an equimolar ratio, into the upper section of column R, these two components advantageously being mixed thoroughly in an upstream mixing chamber. Mixing can be effected, for example, by introducing the reactants into a tank via spray nozzles. This tank simultaneously serves as a pump reservoir for feeding the column.

The temperature in the upper region of the column is adjusted so that most of the reaction mixture is in the liquid phase. The vapor phase is condensed in the conventional manner and recycled in its entirety to the column or mixing chamber.

Below the upper region of the column, the methyl formate vaporizes and thus enters the cooler liquid phase again. The ammonia, which is entrained in solution in the descending liquid, is also driven out of the liquid phase as a result of the increase in temperature, so that virtually no methyl formate or ammonia is left in the middle column section. The advantage of this procedure is that the two products, formamide and methanol, are continuously removed from the reaction equilibrium, as a result of which the conversion to formamide proceeds rapidly and virtually quantitatively.

The mean residence time of the liquid in the upper column section can be set by the height of the weirs on the bubble or valve trays and, together with the residence time in the mixing tank, is preferably from 10 to 60 minutes.

This means that from about 70 to 95% by weight of the total contents of the column are in the upper region.

The methanol vaporizes in the middle to lower region of the column and, according to process step (b), is removed from the column in vaporous form at about the level of trays 1 to 5. This methanol still contains from about 0.3 to 1% by weight of formamide, according to the vapor pressure of formamide.

The vaporous stream of methanol can also be removed directly from the evaporator if this is a twostage evaporator. In the first stage of the evaporator, just the amount of heat required for the amount of methanol to be removed in vaporous form is supplied to the methanol-rich liquid mixture issuing from the column. This amount of heat is about two thirds of the total, the evaporator being at about 95°–98° C. under normal pressure. The remainder of the heat is supplied in the 2nd stage of the evaporator at from 125° to 128° C. The vapor from the 1st stage, which contains less than 1% by weight of formamide, is removed, whilst the vapor from the 2nd stage, containing about 3–5% by weight of formamide, is introduced into the column. As is the case with a side take-off from the lower region of the column, this measure ensures that the methanol vapor removed contains only a little formamide.

In process step (c), the formamide-containing methanol is separated in a column D1 into a top fraction of pure methanol and a bottom fraction of the small amounts of formamide and small amounts of methanol, after which the bottom fraction is recycled to R, preferably somewhat below the side methanol take-off.

The separation operation in D1 present no problems, and packed columns having from 1 to 5 plates are therefore preferred. Instead of a column, it is also possible to use a simple separating vessel for partial condensation of the formamide.

The bottom product from reaction column R substantially consists of formamide, and in addition also contains from about 7 to 15% by weight of methanol. In process step (d), this bottom product is separated, in a column D2 under a pressure of about 30 mbar, into a bottom fraction of pure formamide and a top fraction of methanol. This distillation also prerents no problems, so that a packed column having from 5 to 20 theoretical plates is preferably used.

The nitrogen content of the methanol obtained via columns D1 and D2 is less than 100 ppm. This value is remarkably low, since methanol/formamide mixtures tend to split back into methyl formate and ammonia, so that the methanol obtained by previous processes always contained from 300 to 500 ppm of bonded nitrogen and had to be subjected to expensive purification.

In our own investigations we have found that the establishment of equilibrium of thhe formamide reaction formulated above is accelerated by the presence of ammonia. Accordingly, re-formation of methyl formate and ammonia from methanol and formamide proceeds only very slowly if no ammonia is present. Since almost all the ammonia in the present process is retained in the upper and middle region of the reaction column, no such re-formation can occur, which is the outstanding result of the process according to the invention, apart from the technological advantages.

This results in the requirement, which is easy to fulfil technologically, that the bottom temperatures in R should not exceed or fall below the values given, since at higher temperatures ammonia can be liberated by decomposition of the formamide and at lower temperatures ammonia can pass from the upper region of the column into the lower.

The methanol can be recycled to the methyl formate synthesis stage without further treatment. Since virtually no methanol is lost in the process, it forms a closed circulation around the synthesis stage and the methyl formate aminolysis.

With a view to energy savings, the process according to the invention can be developed further by compressing the vapor to 10-15 bar upstream of the condenser. The condensation temperature thereby rises to values of up to 150° C. At this high temperature, a rapid reaction takes place in the pump reservoir for the column reflux, which simultaneously serves as the mixing tank. If the column is operated under atmospheric pressure, it is possible to utilize the heat at the top to operate the evaporator at the bottom of the column and thus to save a corresponding amount of heating steam. Liquid or vaporous ammonia can be added. Liquid ammonia is preferably used in the procedure with an increased condenser pressure.

The formamide is obtained in virtually quantitative yield and in a purity such that, for most purposes, it does not need further purification.

EXAMPLE 1,100 g of formamide and 312 g of ammonia (molar ratio 1:1) per hour were introduced into the upper region of a 2.5 m high bubble tray reaction column R which was operated under atmospheric pressure, had 10 theoretical plates and was mounted on a packed column having 15 theoretical plates.

The top 10 trays were at 59° to 74° C., all the reactants being predominantly liquid.

The mean residence time of the reactants in this region was about 50 minutes, corresponding to about 80% by weight of the contents of the column being in the upper region. The column was operated under complete reflux.

A vaporous mixture of 517 g of methanol and 3 g of formamide per hour was removed from the column at 98° C. at the level of the 1st tray (counted from the bottom). This mixture was separated, in a short packed column having 8 theoretical plates, into a top fraction of 505 g/h of methanol and a bottom fraction of 12 g/h of methanol and 3 g/h of formamide. The bottom fraction was recycled to the level of the 1st tray in column R. A liquid mixture of 825 g of formamide and 82 g of methanol per hour was removed from the bottom of column R at 128° C. and was separated, in a packed column having 15 theoretical plates, into a top fraction of 82 g/h of methanol and 21 g/h of formamide and a bottom fraction of 804 g/h of formamide. The formamide was >99% pure and the methanol contained less than 100 ppm of nitrogen.

We claim:

1. A process for the continuous preparation of formamide from methyl formate and ammonia, pure methanol being recovered, wherein
    (a) the reaction of methyl formate and ammonia in substantially equimolar quantities is carried out predominantly in the liquid phase in the upper region of a reaction column R having a total of from 15 to 30 theoretical plates, with said reaction column R being operated at a pressure ranging from atmospheric to about 2 bar and wherein a temperature gradient is maintained therein which under atmospheric pressure ranges from 30°-62° C. at the top of said column to 110°-130° C. at the bottom and from 50°-80° C. at the top and 110°-130° C. at the bottom when employing a pressure of about 2 bar,
    (b) the methanol formed in this reaction is removed, together with small amounts of formamide, from the column in vaporous form at the level of plates 1-5 (counted from the bottom),
    (c) the formamide is removed from this methanol/formamide mixture, together with small amounts of methanol, as a bottom fraction in a distillation column D1 and recycled to R, pure methanol is taken off column D1 as a top fraction and recovered, and
    (d) the small amounts of methanol contained in the bottom product from R, which substantially consists of formamide and in this column should be at from 110° to 130° C., are separated off in a distillation colum D2.

2. The process of claim 1, wherein the methyl formate and the ammonia are mixed in a mixing chamber M before entry into the column R.

* * * * *